United States Patent
McDonnell, Jr.

(10) Patent No.: US 10,835,407 B2
(45) Date of Patent: Nov. 17, 2020

(54) ORTHOTIC DEVICE FOR ASSISTING LIMB MOVEMENT

(71) Applicant: Michael T. McDonnell, Jr., Wynnewood, PA (US)

(72) Inventor: Michael T. McDonnell, Jr., Wynnewood, PA (US)

(73) Assignee: Michael T. McDonnell, Jr., Wynnewood, PA (US)

( * ) Notice: Subject to any disclaimer, the term of this patent is extended or adjusted under 35 U.S.C. 154(b) by 717 days.

(21) Appl. No.: 15/448,731

(22) Filed: Mar. 3, 2017

(65) Prior Publication Data

US 2017/0172782 A1 Jun. 22, 2017

Related U.S. Application Data

(63) Continuation-in-part of application No. 14/489,196, filed on Sep. 17, 2014, now Pat. No. 9,585,770, which
(Continued)

(51) Int. Cl.
*A61F 5/00* (2006.01)
*A61F 5/01* (2006.01)
(Continued)

(52) U.S. Cl.
CPC .......... *A61F 5/0127* (2013.01); *A43B 3/0015* (2013.01); *A43B 7/20* (2013.01);
(Continued)

(58) Field of Classification Search
None
See application file for complete search history.

(56) References Cited

U.S. PATENT DOCUMENTS

| 4,573,457 A | * | 3/1986 | Parks | A61F 5/0127 36/102 |
| 6,056,712 A | * | 5/2000 | Grim | A61F 5/0127 602/16 |

(Continued)

OTHER PUBLICATIONS

Yong-Lae Park, Bio-inspired Active Soft Orthotic Device for Ankle Foot Pathologies, 8 pages.
(Continued)

*Primary Examiner* — Kim M Lewis
(74) *Attorney, Agent, or Firm* — Finnegan, Henderson, Farabow, Garrett & Dunner, LLP (57) ABSTRACT

An orthotic device is disclosed. The orthotic device may be adapted to be inserted into a shoe to enable the foot to replicate normal motion so that the user regains substantially normal operation of the foot. The orthotic device may have a frame system formed of a lightweight supportive material and configured to extend along at least the bottom of the user's foot, and an electronically actuated muscle operatively connected to the frame system for expanding and contracting at predetermined levels to adjust the inclination of the user's foot and mimic movement of the foot, when functioning normally. The orthotic device may also have a controller operatively connected to the muscle for transmitting signals corresponding to the predetermined levels to the muscle, and a sensor controlled by the user for actuating the muscle.

19 Claims, 9 Drawing Sheets

Related U.S. Application Data is a continuation-in-part of application No. 13/842,811, filed on Mar. 15, 2013, now Pat. No. 9,480,300.

(51) Int. Cl.
| | |
|---|---|
| *A43B 3/00* | (2006.01) |
| *A43B 7/20* | (2006.01) |
| *A61F 2/50* | (2006.01) |
| *A61F 2/70* | (2006.01) |
| *A43B 13/14* | (2006.01) |

(52) U.S. Cl.
CPC ........... *A61F 5/0113* (2013.01); *A43B 13/141* (2013.01); *A61F 2002/5066* (2013.01); *A61F 2002/704* (2013.01); *A61F 2005/0155* (2013.01)

(56) References Cited

U.S. PATENT DOCUMENTS

| | | | | |
|---|---|---|---|---|
| 6,464,659 | B1* | 10/2002 | DeToro | A61F 5/0195 |
| | | | | 602/23 |
| 7,834,527 | B2 | 11/2010 | Alvarez Icaza Rivera et al. | |
| 8,808,214 | B2* | 8/2014 | Herr | A61B 5/1038 |
| | | | | 602/23 |
| 9,066,818 | B2* | 6/2015 | Pop | A61F 2/64 |
| 2005/0038365 | A1* | 2/2005 | Scott | A61F 5/0113 |
| | | | | 602/23 |
| 2011/0196277 | A1* | 8/2011 | Savard | A61F 5/0127 |
| | | | | 602/28 |
| 2012/0238914 | A1 | 9/2012 | Goldfield et al. | |
| 2014/0088728 | A1* | 3/2014 | Herr | A61F 2/66 |
| | | | | 623/32 |
| 2016/0047160 | A1* | 2/2016 | Huynh | E05F 15/77 |
| | | | | 49/31 |
| 2017/0202724 | A1* | 7/2017 | De Rossi | A61H 3/00 |
| 2017/0319369 | A1* | 11/2017 | Han | A61F 5/0127 |
| 2019/0015284 | A1* | 1/2019 | Horst | A61H 3/00 |

OTHER PUBLICATIONS

Ali Maziz, Knitting and weaving artificial muscles, Science Advances, Jan. 25, 2017; 27 pp., vol. 3, No. 1, e1600327.

* cited by examiner

ORTHOTIC DEVICE FOR ASSISTING LIMB MOVEMENT

PRIORITY

This application is a continuation-in-part of application Ser. No. 14/489,196, filed Sep. 17, 2014, which is a continuation-in-part of application Ser. No. 13/842,811, filed Mar. 15, 2013, both of which are incorporated by reference.

TECHNICAL FIELD

The present disclosure generally relates to an orthotic device adapted to be attached to a limb, particularly a foot, to enable the limb to replicate normal motion so that the user regains substantially normal limb function. The present disclosure has particular utility in addressing gait abnormalities commonly experienced by elderly or those suffering from a myriad of health conditions.

BACKGROUND

A staggering number of people are affected by a gait abnormality characterized by a dropping of the forefoot, referred to as drop foot. This condition is classified as the loss of the ability to move one's foot, either from weakness or paralysis. Individuals suffering from a drop foot condition have difficulty lifting the front part of the foot, causing the foot to hang down and turn inward. In some cases, individuals with drop foot are unable to lift their toes sufficiently while walking, so their toes drag while taking a step. Some lift their leg higher to overcompensate for their inability to control their affected foot. The risk of falling is significantly increased.

The population affected by drop foot condition is significant. Senior citizens represent a growing segment in society as lifespans increase, but many over the age of sixty-five find it difficult to walk three city blocks or one flight of stairs because of an inability to lift their feet from weakness, paralysis, or chronic health issues. In fact, drop foot is a common side effect experienced by patients recovering from stroke, multiple sclerosis, spinal cord injury, Parkinson's disease, Charcot-Marie-Tooth disorder, diabetes, and fibula fracture, to name a few.

In the not too distant past, people with gait difficulties, particularly the elderly, were left behind. Even today, improvements for assisting individuals with impaired gait have failed to offer a user-friendly orthotic device, particularly one that is not bulky or unattractive.

There are static orthotic braces and actuating nerve-stimulating orthotics called Functional Electrical Stimulators (FES). The FES systems include Bioness, which is an orthotic that is wrapped around the portion of the leg right below the knee. It is placed on the personal nerve, which provides motion to the foot and ankle, but does not help muscular drop foot. Another FES System is WalkAide. Like Bioness, it shocks the personal nerve and is only useful for severe nerve damage.

Examples of static orthotic products include Molded Ankle Foot Orthotics (MAFO) and Silicone Ankle Foot Orthotics (SAFO). A MAFO orthotic is a rigid or semi-rigid brace, while the SAFO orthotic consists of a silicone wrap. Static systems such as the SAFO and MAFO, however, typically limit ankle movement and do not assist the patient in lifting the heel and/or toe upward while taking a step. Other drawbacks in conventional devices include the bulky and/or undesirable appearance, causing many to discontinue use and remain sedentary.

In view of the foregoing, a need exists for improved orthotic devices, not merely to address drop foot condition, but which also takes into consideration concealing the device from normal view.

SUMMARY

In one aspect, the present disclosure is directed to an orthotic device adapted to be inserted into a user's shoe to enable the foot to initiate normal motion so that the user regains substantially normal functioning of the foot. The orthotic insert also enables the insert to minimize the likelihood of falling by inclination of the toe as the user approaches steps, curbs, door thresholds, etc. The orthotic device may include a frame system formed of a lightweight supportive material and configured to be inserted into a user's shoe, and an electronically actuated muscle operatively connected to the frame system for expanding and contracting at predetermined levels to mimic movement of the foot and lifting the user's toes, when functioning normally. The orthotic device may further include a controller operatively connected to the muscle for transmitting signals corresponding to the predetermined levels to the muscle, and a sensor controlled by the user for actuating the muscle.

In another aspect, the present disclosure is directed to an orthotic insert capable of being concealed from normal view within a shoe.

DETAILED DESCRIPTION

Figure 1:
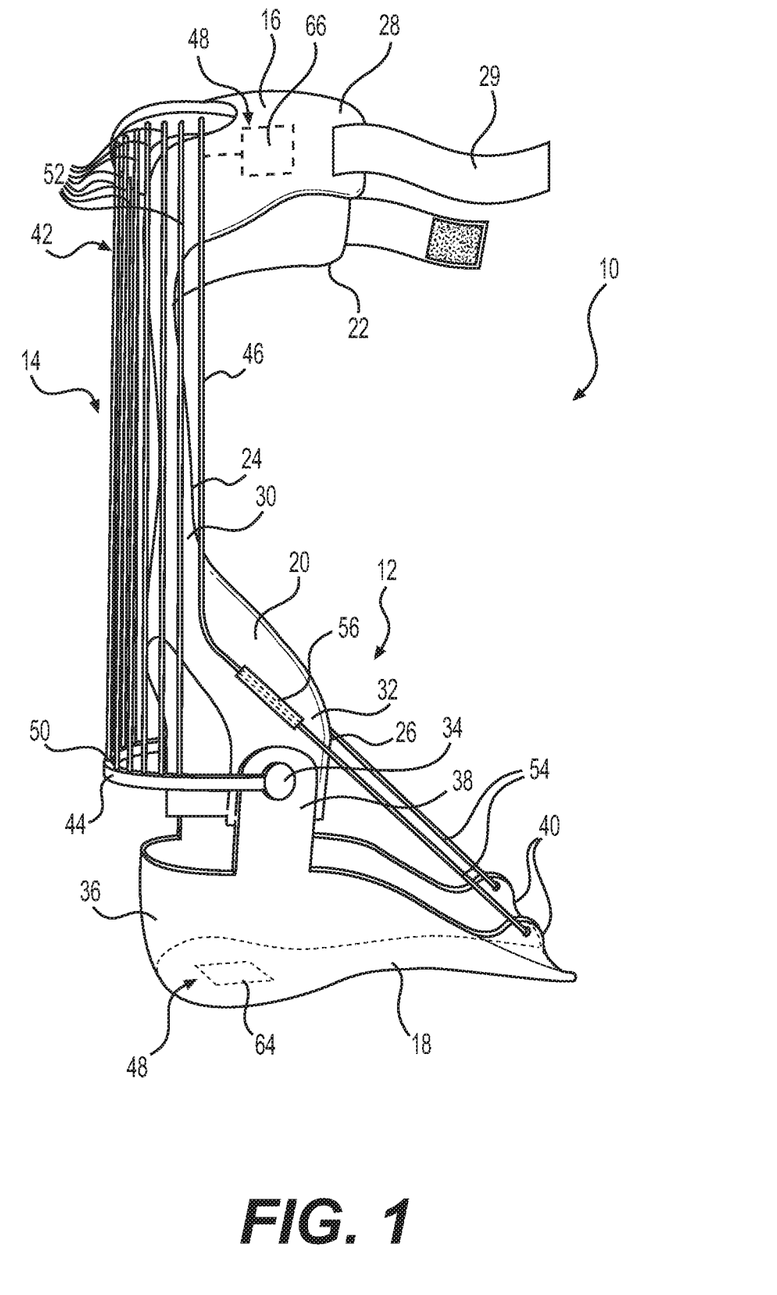
FIG. 1 includes a schematic illustration of an exemplary orthotic device of the present disclosure.

FIG. 1 illustrates an exemplary disclosed orthotic device 10 including a frame system 12 and an actuating system 14. Orthotic device 10 may be configured for attachment to a user's lower leg to assist with movement of the leg. Frame system 12 may provide structural support for a user's foot, while actuating system 14 may be configured to replicate normal motion of the user's leg by moving frame system 12. As discussed in more detail below, actuating system 14 may be configured to transmit forces to and from the user through frame system 12, thereby assisting the user with walking and rehabilitation. In addition, frame system 12 and actuating system 14 may be sized and shaped to substantially conform to the user's lower leg and foot, such that orthotic device can easily be concealed (e.g., in a stocking or sock, and/or beneath a user's shoe and pant leg).

While orthotic device 10 is depicted and described in relation to a user's leg and foot, it should be understood that some of the disclosed embodiments may be adapted for use with other limbs and/or body parts. For example, orthotic device 10 may be adapted for use with a user's arm, wrist, and/or hand, including a frame system 12 to support the limb and an actuating system 14 to control movement of frame system 12 and the associated limb. For example, frame system 12 may be adapted to fit to a user's forearm and hand, while actuating system 14 provides pivotal movement, such as to mimic normal motion of the user's wrist. Similarly, it should be understood that some of the disclosed embodiments may be adapted for use with a limb of an animal, such as a horse. For example, frame system 12 may be adapted for attachment to an animal's leg and foot, providing the animal with assistance with walking and/or rehabilitation.

As shown in FIG. 1, frame system 12 may include an upper frame 16 and a lower frame 18. Upper frame 16 may include a leg holder 20 configured to be secured to a portion of the user's leg. Leg holder 20 may be securable to a user's lower leg, for example, below the knee. In one embodiment, leg holder 20 may include an upper attachment portion 22, a support portion 24, and a connection portion 26.

Upper attachment portion 22 may extend partially or completely around a user's leg to anchor upper frame 16 to the user. For example, upper attachment portion 22 may include a U-shaped cuff 28 configured to fit snugly and securely around at least a back side of a user's lower leg. In some embodiments, upper attachment portion 22 may include a securing mechanism, such as a strap 29 configured to wrap around a front side of the user's lower leg and be secured in position (e.g., via Velcro®, snaps, buckles, etc.). It should be understood, however, the upper attachment portion 22 may include any configuration that enables leg holder 20 to be securely attached to an upper portion of the user's lower leg.

Support portion 24 may be a rigid support member extending downwardly from upper attachment portion 22. As shown in FIG. 1, support portion 24 may be a single elongated member 30 configured to be positioned adjacent a back side of the user's lower leg. In some embodiments, elongated member 30 may be curved around a longitudinal axis to conform to the user's leg. Support portion 24 may provide strength and rigidity to leg holder 20, allowing upper frame 16 to act as an anchor on the user's lower leg that remains stationary to support relative movement of lower frame 18. It should be understood that the embodiment of support portion 24 depicted in FIG. 1 is exemplary, and that other configurations are possible. For example, a pair of elongated members 30 may be positioned on opposite sides of leg holder 20, configured to be positioned at opposing sides of the user's lower leg (e.g., lateral sides, front/back, etc.).

Connection portion 26 may connect upper frame 16 to lower frame 18. In an exemplary embodiment, connection portion 26 may extend from support portion 24 to opposing sides of leg holder 20. In the embodiment of FIG. 1, for example, connection portion 26 may include a yoke 32 configured to extend from a back side of the user's leg to the sides around the ankle. As will be described in more detail, connection portion 26 may be pivotally connected to lower frame 18 via a pivot mechanism 34.

In some embodiments, leg holder 20 may include a shape and dimensions tailored for an individual user. Upper attachment portion 22, support portion 24, and connection portion 26 may be formed as a unitary member from a lightweight, supportive material, such as a reinforced plastic material (e.g., a fiber-reinforced polymer). In other embodiments, upper attachment portion 22, support portion 24, and/or connection portion 26 may be formed as separate components and secured to each other (e.g., via fasteners).

Lower frame 18 may include a heel cup 36, a pair of first connectors 38 and a pair of second connectors 40. Heel cup 36 may be a cup-like support portion configured to receive at least a portion of the user's foot. For example, heel cup 36 may be configured to receive at least a heel portion of the user's foot. Heel cup 36 may be substantially shaped to match the contours of the user's foot such that the user's foot fits snugly within heel cup 36. For example, heel cup 36 may be custom-molded from a polymer and/or fiber-reinforced material to substantially match the shape of a user's foot. In other embodiments, heel cup 36 may be generally shaped to match an average foot.

First connectors 38 may extend from heel cup 36 and secure heel cup 36 to leg holder 20 via pivot mechanism 34. Pivot mechanism 34 may include, for example, a pin extending from first connectors 38 and into an aperture in connection portion 26 of leg holder 20, or vice versa. In this way, heel cup 36 may pivot relative to leg holder 20.

First connectors 38 may extend to an area adjacent to a user's ankle when orthotic device 10 is worn, such that pivot mechanism 34 is substantially aligned with the pivot point created by the user's ankle. In this way, during use, pivoting of heel cup 36 relative to leg holder 20 may cause corresponding pivotal movement of the user's foot via the user's ankle.

Second connectors 40 may include one or more connection mechanisms configured to be secured to a portion of actuating system 14 such that movement of a component of actuating system 14 causes movement of second connectors 40. In an exemplary embodiment, movement of second connectors 40 may cause heel cup 36 to rotate about pivot mechanism 34, such as to lift the user's toes relative to the user's heel.

In one embodiment, heel cup 36, first connectors 38, second connectors 40, and/or a pivot member 44 (described in more detail below and includes pivot members 44a (FIG. 3) and 44b (FIG. 4)) may be formed as a unitary structure from a lightweight, supportive material, such as a reinforced plastic material (e.g., fiber-reinforced plastic). In other embodiments, first connectors and/or second connectors may be separate components from heel cup 36 and secured thereto. For example, first connectors and/or second connectors may be tabs secured at various locations around heel cup 36. The tabs may be rigid and/or flexible (e.g., rigid polymer, flexible polymer, fabric, etc.). Heel cup 36 may be sized and shaped to fit within a normal-sized shoe, such that the user's foot and heel cup 36 may fit comfortably within the shoe.

Suitable materials for frame system 12 include carbon fiber, aramid fibers, resin, including resin impregnated glass, and polymers such as polyethylene or polyurethane. In some embodiments, upper frame 16 may include one or more materials different from lower frame 18. For example, upper frame 15 may comprise a substantially rigid material, such as, for example, carbon fiber, and lower frame 18 may comprise a substantially flexible material configured to substantially mold to a patient's foot, including but not limited to, thermoplastic resin, natural and man-made rubbers, and cellular foam. It is further contemplated that heel cup 36 may be sufficiently flexible to flex upward and downward with a user's forefoot when walking.

Figure 6:
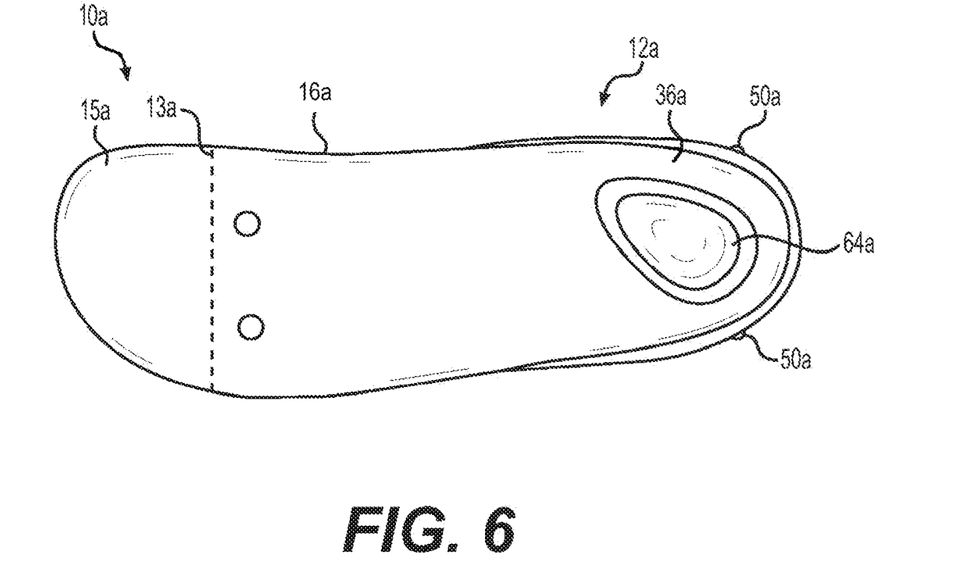
FIG. 6 is a top plan of substantially flexible orthotic insert of the present disclosure.
Figure 7:
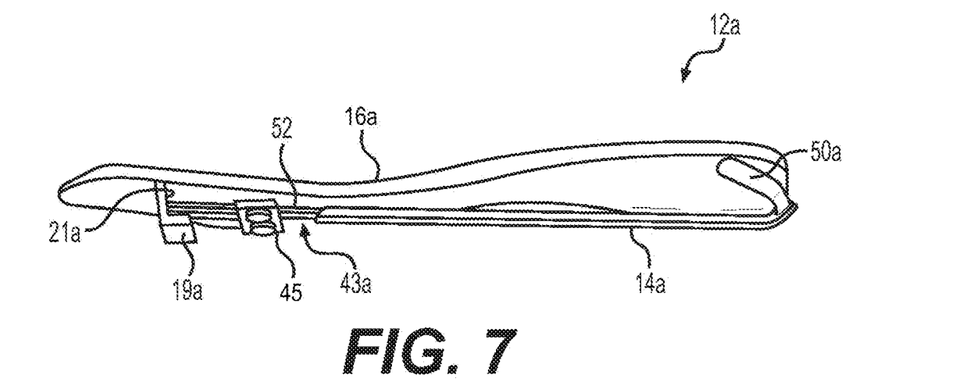
FIG. 7 is a side view of a to portion with attached electroactive fibers of the substantially flexible orthotic insert of the present disclosure.
Figure 8:
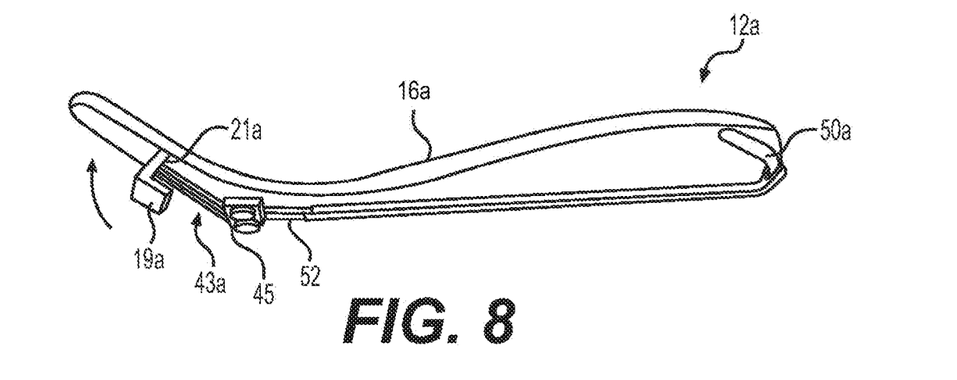
FIG. 8 is a side view of the orthotic insert of FIG. 7 with a toe portion raised.
Figure 9:
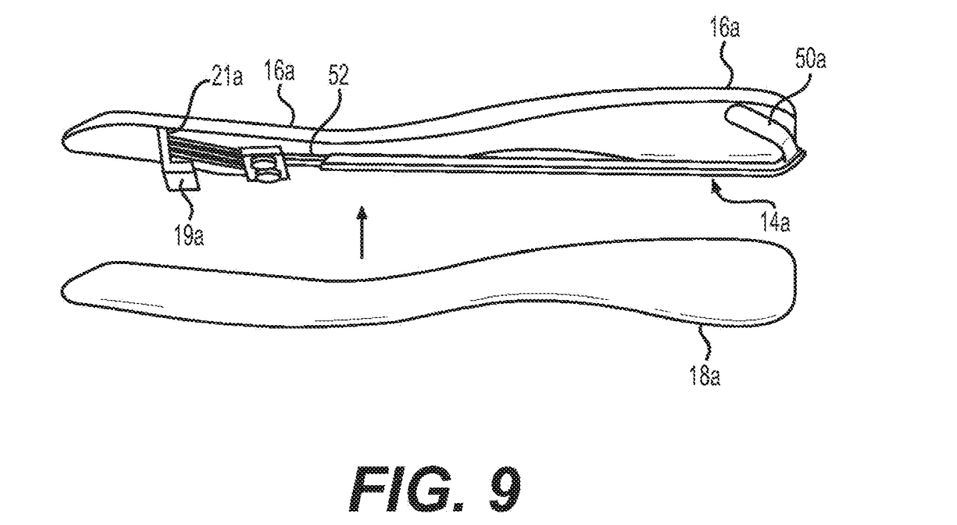
FIG. 9 is an exploded side view of the orthotic insert of FIG. 7 featuring a bottom portion that is attached to the base of the top portion.
Figure 10:
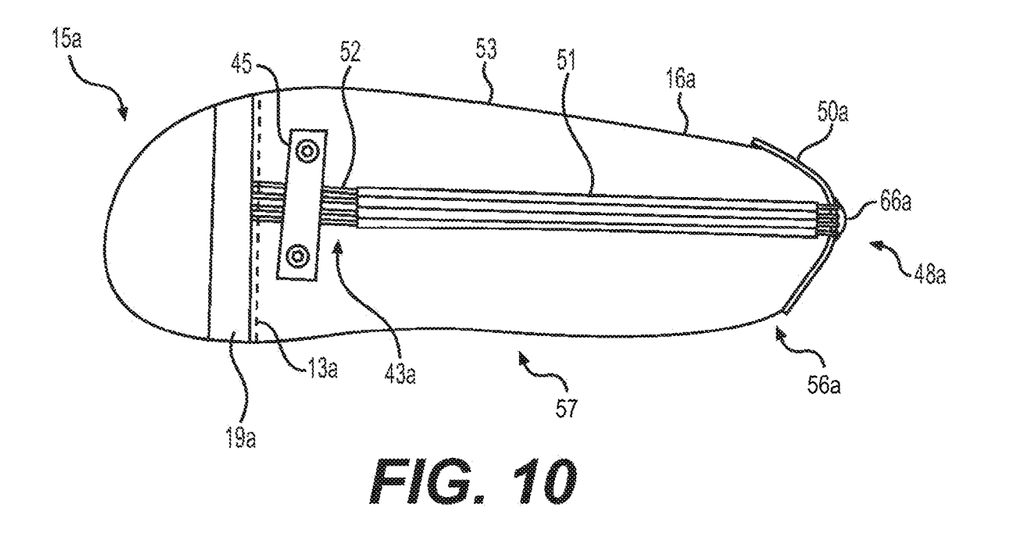
FIG. 10 is a bottom plan view of the electroactive fibers disposed along the base of the top portion of the substantially flexible orthotic insert of the present disclosure.
Figure 11:
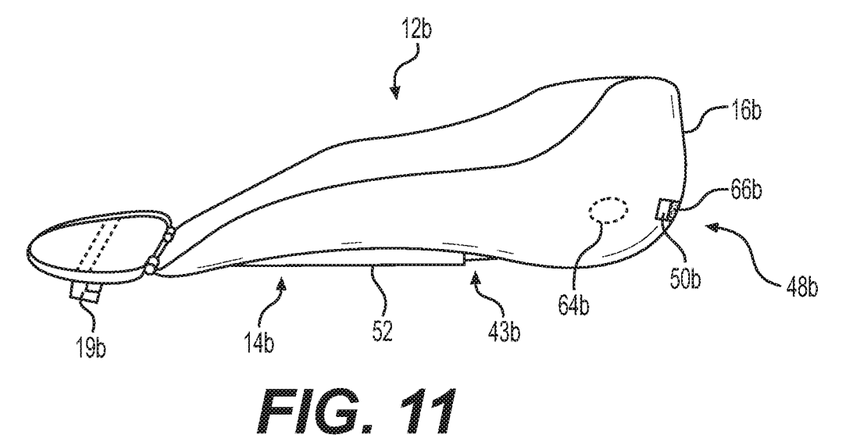
FIG. 11 is a perspective view of a substantially rigid orthotic insert of the present disclosure.
Figure 12:
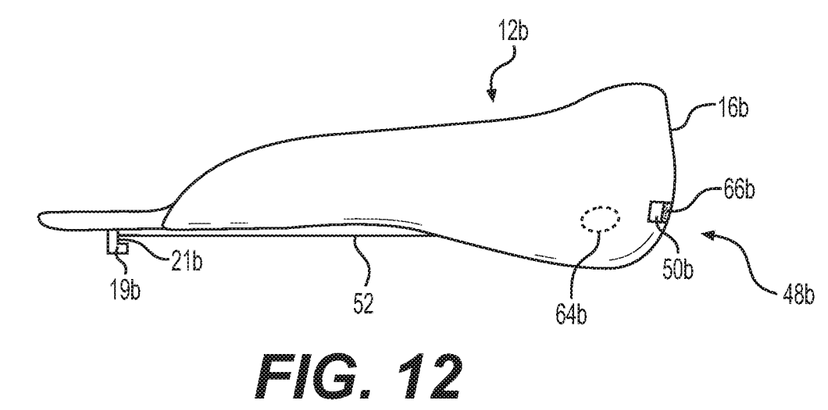
FIG. 12 is a side view of the substantially rigid orthotic insert of the present disclosure.
Figure 13:
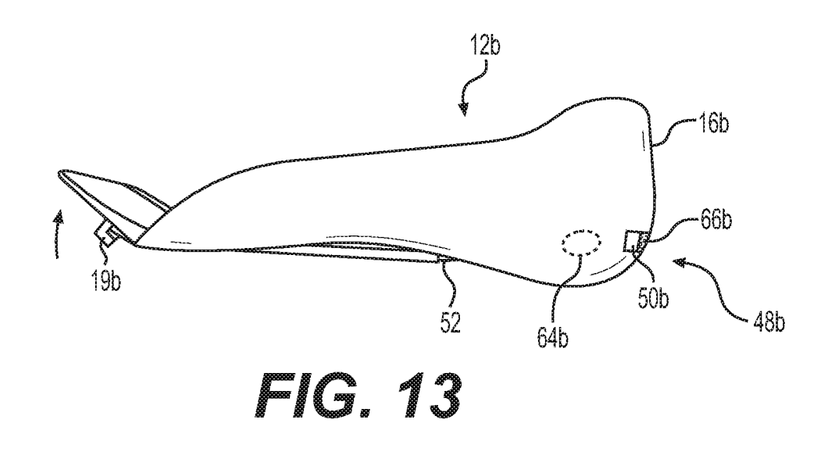
FIG. 13 is a side view of the orthotic insert of FIG. 12 with a toe portion raised.
Figure 14:
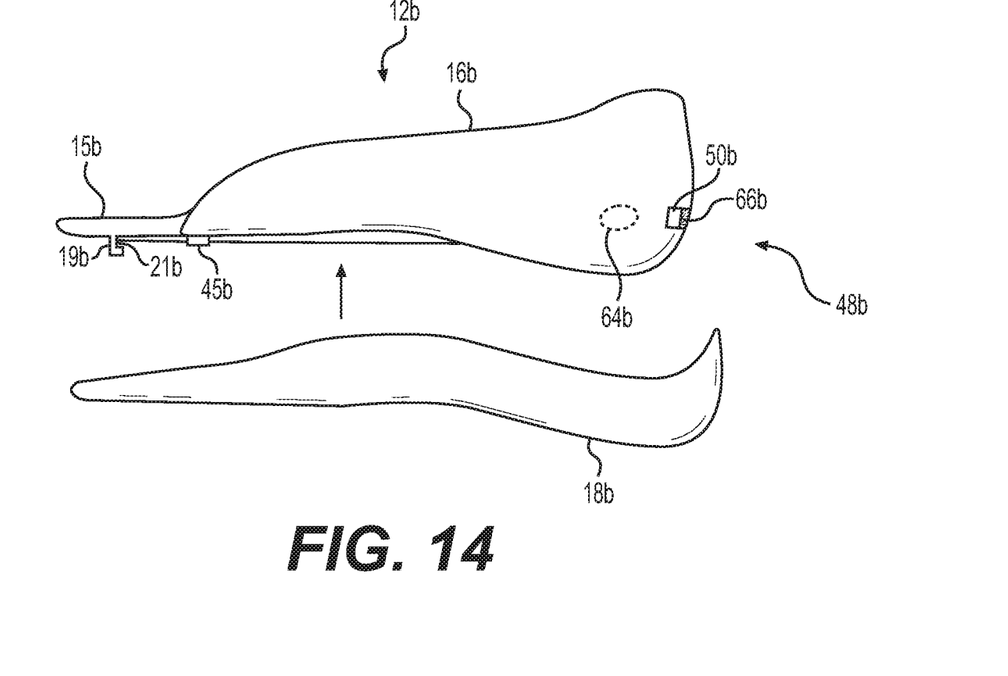
FIG. 14 is an exploded side view of FIG. 12 featuring a bottom portion that is attached to the base of the top portion.
Figure 15:
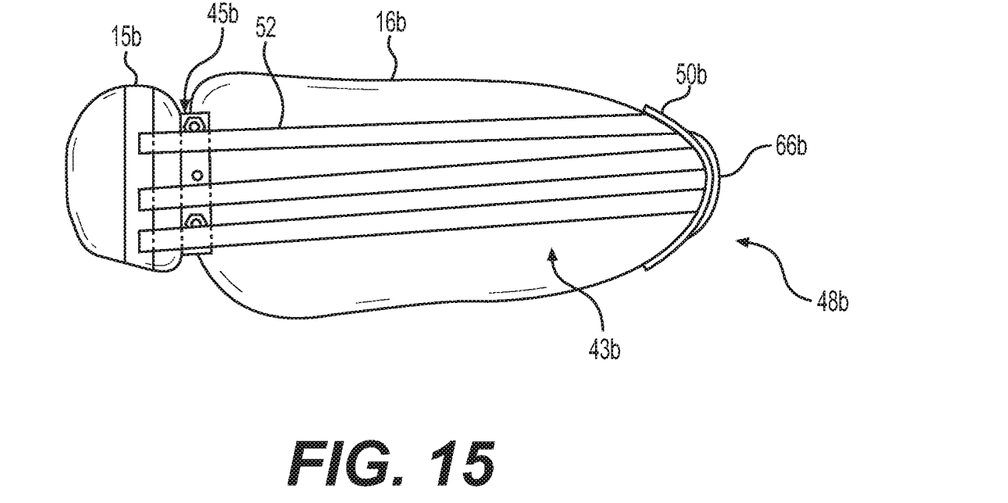
FIG. 15 is a bottom plan view of the electroactive fibers disposed along the base of the top portion of the substantially rigid orthotic insert of the present disclosure.

The present invention also includes an exemplary orthotic device 10*a* having a frame system 12*a*, 12*b* adapted to be configured to be inserted into a shoe, boot, sneaker or the like. In the embodiment shown in FIGS. 6-10, the frame system 12*a* may be formed of lightweight material configured to extend along the bottom of a user's foot. The frame system 12*a* preferably includes an upper frame 16*a* and a lower frame 18*a*, in which an actuator system 43*a*, namely an electronically actuated artificial muscle, are actuator strands 52 (FIG. 2) interposed and sandwiched between the upper frame 16*a* and the lower frame 18*a*. The actuator strands 52 are surrounded by a rigid sheath 51, as shown in FIG. 10, for protection from compression or other damage. Preferably, the lower frame 18*a* is formed of a substantially rigid material and the upper frame is formed of a flexible material, such as high density foam. Preferably, the upper frame 16*a* is secured to the lower frame 18*a* at least along the perimeter of the upper frame 16*a* between the heel and a sear line 13*a* near the toe portion 15*a* of the orthotic insert, thereby creating a pocket around the toe 15*a*. The sear line 13*a*, as shown in FIG. 6, enables the front portion of the upper frame 12*a* to be biased such that the front portion is easy to bend upward, not down, while normally being substantially flat. The upper frame 16*a* of the frame system 12*a* includes an integrally formed downward projection 19*a* forming a channel 21*a* beneath the toe portion 15*a*. The actuating strands 52 are attached to a connector 50*a* at the heel, extended into a sheath 51 along the heel portion 56*a* and the midfoot portion 57 (FIG. 10), and through guide member 45*a* for engagement with the downward projection 19*a* to incline and lower the toe portion 15*a* in response to signals from controller 66*a*. The downward projection 19*a* could have various shapes and forms that facilitate contact with the actuating strands 52, to adjustably position the toe portion 15*a*.

The present invention also includes an exemplary orthotic device 10*b* having a frame system 12*b* adapted to be configured to be inserted into a shoe, boot, sneaker or the like. In the embodiment shown in FIGS. 11-15, the frame system 12*b* may be formed of a lightweight, substantially rigid material, such as polyethylene or polypropylene, configured to envelop the bottom, sides and heel of a user's foot. The frame system 12*b* may include an upper frame 16*b* and a detachable lower frame 18*b*, in which an actuator system 43*b*, which is an electronically actuated electronic muscle, are actuator strands 52*b* (FIG. 2) interposed between the upper frame 16*b* and the lower frame 18*b*, which are spaced to protect the actuator strands 52 from compression or other damage. The upper and lower frames 16*b*, 18*b*, form a guide member 45 proximate the toe portion 15*b* of the upper frame 16*b*. The toe portion 15*b*, which is pivotally connected to the upper frame 16*b*, normally lies flat but is adapted to be raised upward. The upper frame 16*b* of the frame system 12*b* includes a rigid downward projection 19*b* forming a channel 21*b* beneath the toe portion 15*b*. The actuator strands 52 are attached at one end to a connector 50*b* along the heel. The actuator strands 52 extend from the connector 50*b* between the upper frame 16*b* and lower frame 18*b*, and are aligned within a guide member 45 for engagement a channel 21*b* along with the downward projection 19*b* to incline and lower the toe portion 15*b* in response to signals from controller 66*b*. The downward projection 19*b* could have various shapes and forms that facilitate contact with the actuating strands 52, to adjustably position the toe portion 15*b*.

Actuating system 14 in FIGS. 1-5 may be connected to frame system 12 to cause heel cup 36 to rotate about pivot mechanism 34. In an exemplary embodiment in FIGS. 1-5, actuating system 14 may include a first actuator 42, a pivot member 44, a second actuator 46, and a control system 48. First actuator 42 may be connected between leg holder 20 and pivot member 44, which may be fixedly attached to heel cup 36 at first connectors 38. Second actuator 46 may be connected between leg holder 20 and second connectors 40. First actuator 42 and second actuator 46 may each be configured to extend and contract at predetermined levels to cause first connectors 38 and second connectors 40, respectively, to move, thus causing heel cup 36 to rotate about pivot mechanism 34 relative to leg holder 20. Control system 48 may control actuating movement of first actuator 42 and second actuator 46 shown in FIGS. 1-5.

As shown in FIG. 1, pivot member 44 may be a U-shaped connector 50. Connector 50 may include end portions configured to be fixedly secured to first connectors 38 and thus pivotally connected to connection portion 26 of leg holder 20 via pivot mechanism 34. In this way, connector 50 may rotate relative to leg holder 20, causing corresponding rotation of heel cup 36. Connector 50 may be formed from a durable material (e.g., a rigid plastic material). In some embodiments, connector 50 may be integrally formed with heel cup 36.

First actuator 42, second actuator 46 and actuators 43*a*, 43*b* may be electronically-actuated artificial muscles configured to mimic the function of real muscles. For example, each of first actuator 42 and second actuator 46 may be configured to contract and extend to adjust a length thereof, thereby creating a pulling force sufficient to rotate heel cup 36 about pivot mechanism 34.

In the exemplary embodiments, first actuator 42 and second actuator 46 (FIGS. 1-5), and actuating systems 14*a*, 14*b* (FIGS. 6-15), may include electroactive polymer fibers, such as those disclosed in U.S. Pat. No. 7,834,527, which is hereby incorporated by reference into the present disclosure. Similarly, actuating systems 14, 14*a* and 14*b* (FIGS. 6-15) may include electroactive polymer fibers, such as those disclosed in U.S. Pat. No. 7,834,527, or polypyrrole products, which are particularly suitable for low voltage applications as in the present invention. Textile products coated with polypyrrole, as described in Science Advances 25 Jan. 2017, Vol. 3, No. 1, e1600327, which is also incorporated by reference in the present disclosure. In this embodiment, cellulose yarn is coated with polypyrrole, a flexible electroactive polymer. When a low voltage is applied to the electroactive polymer, it increases in volume, causing the yarn fibers to increase in length. When the electric current is switched off, the fibers retract back to their original length. In the embodiments featured in FIGS. 6-15, control system 48a, 48b may control actuating movement of actuating system 14a, 14b.

As shown in FIG. 1, first actuator 42 may include a plurality of actuator strands 52 connected between upper attachment portion 22 and connector 50. Actuator strands 52 may be dispersed around connector 50 (as shown in FIG. 1) or may be consolidated at one or more locations. Second actuator 46 may include one or more actuator strands 54 connected between leg holder 20 and one of second connectors 40. In some embodiments, first connectors 38 may each include a channel 56 attached to leg holder 20 and configured to receive one or more strands 54 therethrough to route the strand(s) to second connector 40.

Figure 2:
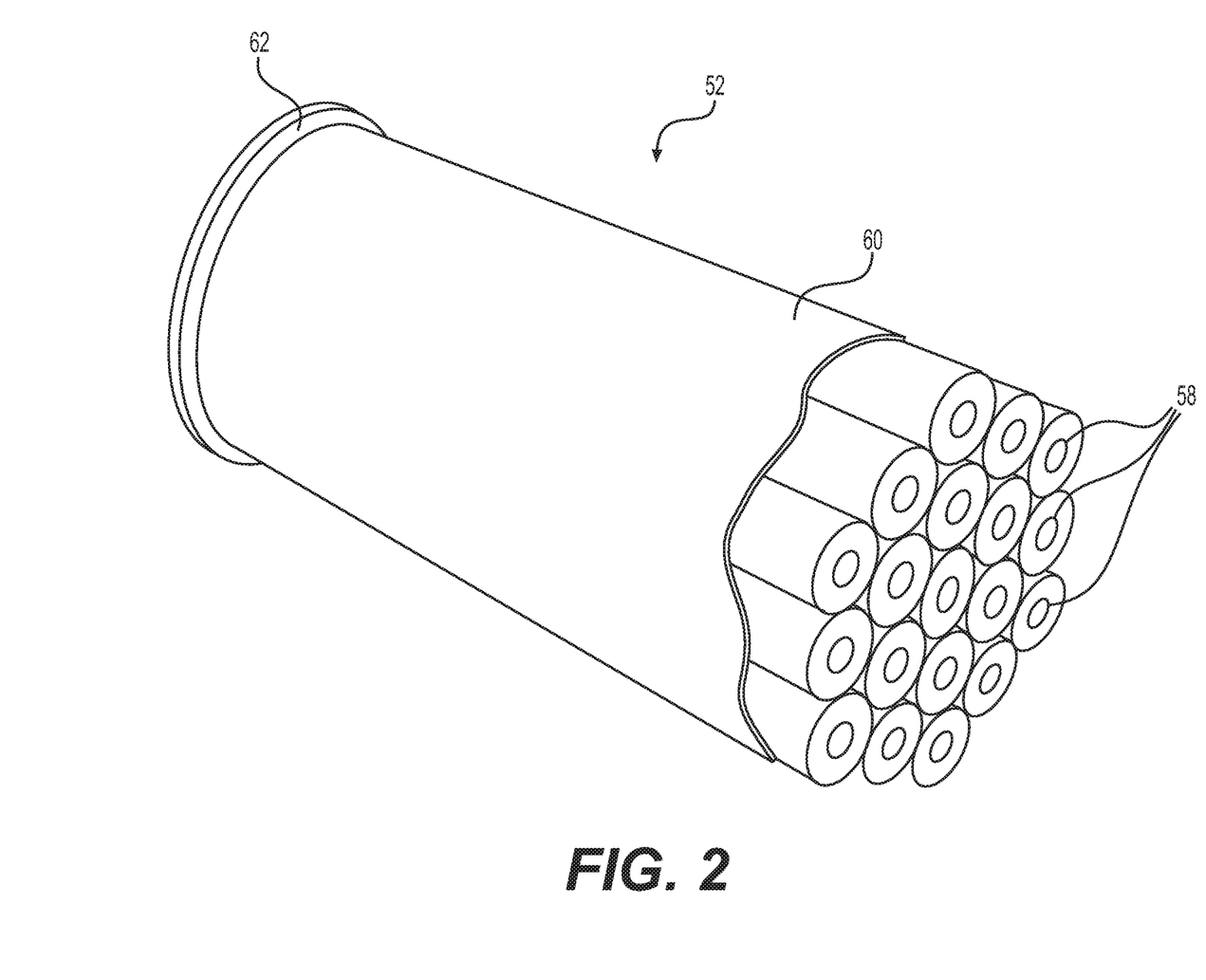
FIG. 2 includes an illustration of an exemplary electronically actuated muscle that may be used in conjunction with the orthotic device of FIG. 1.

FIG. 2 depicts an exemplary actuator strand 52 for the embodiments in FIGS. 1-15 in more detail, and, therefore, the alphanumeric identifiers "a" and "b" associated with the embodiments featured in FIGS. 6-10 and 11-15, will not be included with respect to the features in FIG. 2. As shown in FIG. 2, each actuator strand 52 may include a bundle of electroactive polymer fibers 58 enclosed within an outer sleeve 60. Each fiber 58 may be an elongated, hollow structure formed from an electroactive polymer material. An inner electrode may be positioned within the hollow interior of each fiber 58 and an outer electrode may be positioned around the exterior of the fibers 58 and within outer sleeve 60. In an exemplary embodiment, the inner and outer electrodes may be a liquid, such as water, although other electrode materials are possible. For example, the electrode material may be a polymer configured to extend and contract with fibers 58. End caps 62 (only one shown) may be secured to opposing ends of outer sleeve 60, enclosing fibers 58 and the inner and outer electrodes (e.g., water other fluid) therein.

The electroactive polymer material may be a polymer material wherein upon application of an electric potential between the inner and outer electrodes, the electroactive material is deformed. For example, upon application of a voltage to the outer electrode surrounding polymer fibers 58, fibers 58 may deform by extending in length. Upon removal of the voltage, fibers 58 may return to their original length. In this way, first actuator 42 and second actuator 46, and the actuators 43, 45 illustrated in FIGS. 6-10 and 11-15, can be controlled through selective application and/or removal of a voltage potential. In an exemplary embodiment, control system 48 may be configured to selectively control first actuator 42 and second actuator 46 in this manner. Similarly, control system 48a, 48b may control the actuator strands 52a, 52b to raise the user's toes and assist moving the foot forward.

In an exemplary embodiment, the fibers 58 may be sufficiently thin such that deformation is possible at relatively low voltages. For example, the fibers may be configured such that a deformation occurs at or below an application of 48 V. This amount of voltage may allow activation and deactivation of fibers 58 (and thus strands 52, 54), without significant risk of injury to the user.

Control system 48 may include at least one sensor 64, 64a, 64b and at least one controller 66, 66a, 66b. Sensor 64, 64a, 64b may include one or more sensors in communication with frame system 12, 12a, 12b, respectively, and configured to detect a parameter and generate a signal based on the parameter, such as to cause one or more of first actuator 42 and second actuator 46 to contract and/or extend at predetermined levels. Controller 66 may be operatively connected to sensor 64, 64a, 64b for receiving signals indicating predetermined levels of contraction and/or extension. Controller 66 may also be operatively connected to actuators 42, 46 for transmitting signals corresponding to the predetermined levels to actuators 42, 46. The same is true with respect to the embodiments in FIGS. 6-15, and actuators 43a, 43b.

Sensor 64, 64a, 64b may be a motion sensor. For example, sensor 64, 64a, 64b may detect a change in foot motion or orientation to determine if a user is walking with a substantially normal gait. In some embodiments, sensor 64, 64a, 64b may be configured to detect gait sequence, gait speed, the location of a foot in relation to the user's body or ground, the angle of the foot, the foot placement, etc. For example, sensor 64, 64a, 64b may be configured to detect when a user's foot strikes the ground and the foot placement on the ground. Additionally or alternatively, sensor 64, 64a, 64b may be configured to detect a position of a user (or a user's body part, such as to determine whether the user is standing upright, bending, lifting one or more arms, etc.) or a change in acceleration of the user.

In an exemplary embodiment, sensor 64 may be positioned in proximity to the user's foot and to first and second actuators 42, 46, and sensor 64a, 64b may be positioned in proximity to the user's foot and actuators 14a, 14b. As shown in FIG. 1, for example, sensor 64 may include a sensor pad disposed on a foot-engaging surface 68 of heel cup 36. In another embodiment, sensor 64, 64a, 64b may be additionally or alternatively disposed proximate to the user's other leg and/or foot (e.g., inside a shoe worn by the user's other leg, such as a user's good leg.) In other embodiments, sensor 64, 64a, 64b may be disposed at various other positions on a user including, for example, a user's leg, knee, ankle, or any position on the user's body. It is further contemplated that sensors 64, 64a, 64b may be disposed at more than one location on a user. For example, in one embodiment, sensor 64 may include one or more sensors on heel cup 36 and one or more sensors inside a shoe worn by the user's other foot (e.g., a "good" foot that does not need to use orthotic device 10). Similarly, in the embodiments shown in FIGS. 6-15, sensor 64a, 64b may include one or more sensors on the frame system 12a, 12b and one or more sensors inside a shoe worn by the user's other foot.

In an exemplary embodiment, sensor 64, 64a, 64b may be configured to convert changes in mechanical force to changes in electrical signals. For example, sensor 64, 64a, 64b may include switches, strain gauges, inclinometers, or accelerometers. Additionally, sensor 64 may include one or more wireless components, such as a key fob, configured to remotely communicate with frame system 12, 12a, 12b or controller 66, 66a, 66b. In some embodiments, sensor 64 may include a pressure pad comprising a plurality of inflatable pockets filled with liquid or air. The pockets may be opened or closed, allowing for inflation and deflation of the liquid and air, depending on the placement of a foot during a gait cycle. For example, a foot strike may increase the pressure within the inflatable pockets, while a step off the ground may decrease the pressure. Sensor 64 may measure the air or liquid pressure within each inflatable pocket, and may convert the pressure measurement into an output signal.

In some embodiments, sensor 64, 64a, 64b may include one or more sensors configured to detect a user's body motion or orientation to determine the walking intention of the user. For example, sensor 64, 64a, 64b may be configured to detect when a user lean forwards, leans to the right or left, a pivot in the user's hips left or right, a pivot in the user's torso left or right, etc. In one embodiment, a lean forward by a user may indicate the user's intention to walk faster. In another embodiment, a pivot of the user's hips to the right may indicate the user's intention to turn to the right. Sensor 64, 64*a*, 64*b* may be disposed at various positions on the user's body or in proximity to the user, and may include, for example, an inclinometer or accelerometer. In one embodiment, one or more sensors 64, 64*a*, 64*b* may be configured to detect a user's body motion or orientation may be disposed on the user's legs and arms.

Controller 66, 66*a*, 66*b* may receive an output signal from sensor 64, 64*a*, 64*b*, and may process the signal to control the orientation of first and second actuators 42, 46 (FIGS. 1-5), or actuating system 14*a*, 14*b*, (FIGS. 6-15) as described in greater detail hereinafter. In one embodiment, controller 66, 66*a*, 66*b* may be a micro electronic circuit including a processor having one or more processing devices configured to carry out a process for activating orthotic device 10, 10*a*, 10*b*. For example, the processor may be configured to receive preprogrammed input from sensor 64, 64*a*, 64*b* and monitor first and second actuators 42, 46, or actuators 43*a*, 43*b*. In one embodiment, the processor may determine when to activate and de-activate first and second actuators 42, 46, or actuators 43*a*, 43*b*. For example, the processor may determine when to extend or contract first and second actuators 42, 46 to a predetermined level, such as by selective application of a voltage pulse to strands 52 and 54. Controller 66 may also include one or more wireless components configured to wirelessly communicate with first and second actuators 42, 46 and/or sensor 64. Similar features apply with respect to controller 66*a*, 66*b*, actuating systems 14*a*, 14*b* and/or sensors 64*a*, 64*b*.

Control system 48 may further include a power source configured to supply power to actuator system 14, 14*a* and 14*b*. In some embodiments, the power source may be a portable battery. In some embodiments, the power source may be secured to frame system 12, for example, to leg holder 20 or heel cup 36. In other embodiments, the power source may be positioned remotely from orthotic device 10, 10*a* and 10*b* (e.g., be worn on a belt around a user's waist or arm. In some embodiments, the power source may include one or more power sources, for example, a first power source coupled to sensor 64 and a second power source coupled to first and second actuators 42, 46, or actuating system 14*a*, 14*b*.

In some embodiments, control system 48 may be configured to operate in one or more of a plurality of modes. For example, control system 48 may include algorithms (e.g., software instructions) that may be executed (e.g., by controller 66, 66*a*, 66*b*) to cause orthotic device 10 to operate in a walking mode or a rehabilitation mode. In an exemplary embodiment, the walking mode may include operations described above, in which sensor 64, 64*a*, 64*b* and controller 66, 66*a*, 66*b* communicate with each other to assist the user with walking. The rehabilitation mode, on the other hand, may include operations in which first and second actuators 42, 46 and actuators 43*a*, 43*b* extend and contract to cause pivoting the heel or raise the toe in a situation in which the user is not walking (e.g., when the user is inactive, resting, etc.). For example, the user's foot may be raised in the air while first and second actuators 42, 46 extend and retract to move the user's foot through a range of motion that includes sequentially lifting the user's heel and lifting the user's forefoot (e.g., toes). The rehabilitation mode may stretch the user's muscles, helping to keep the muscles active and prevent atrophy.

Figure 3:
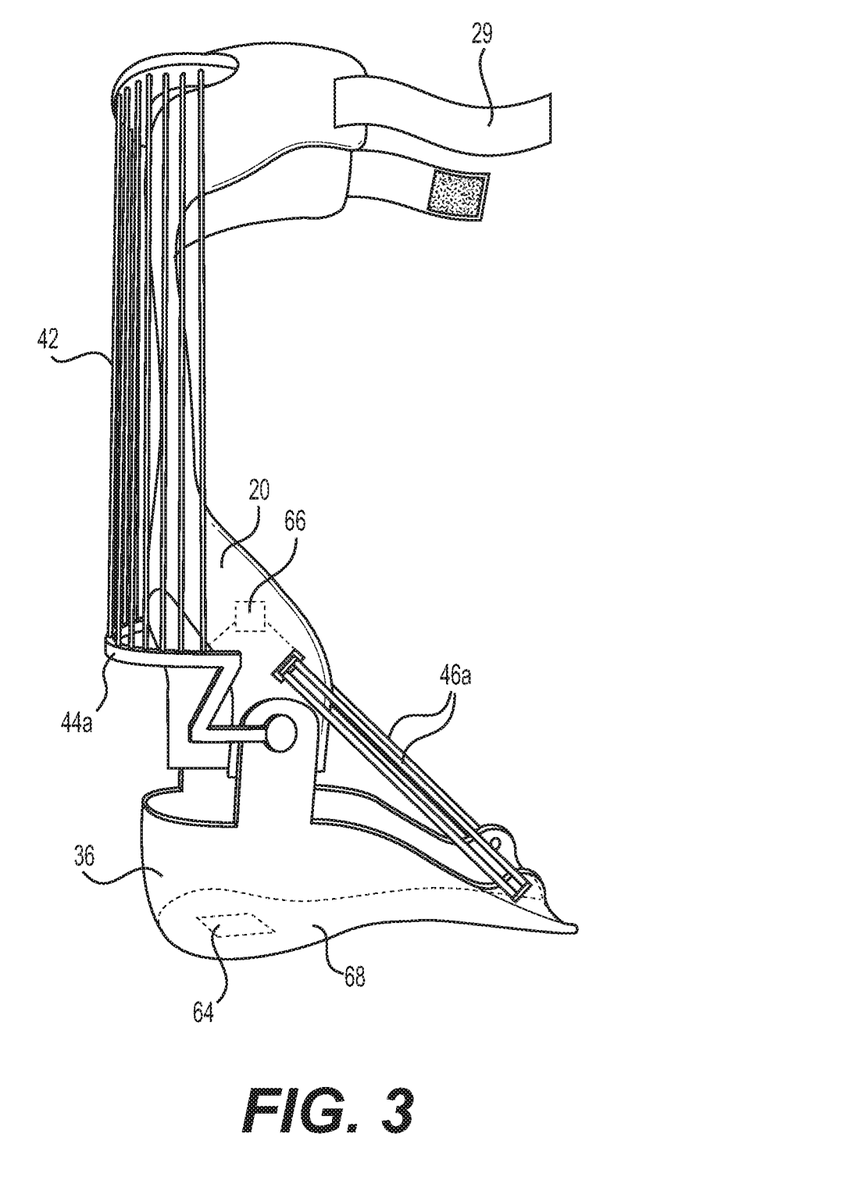
FIG. 3 includes another schematic illustration of another exemplary orthotic device of the present disclosure.
Figure 4:
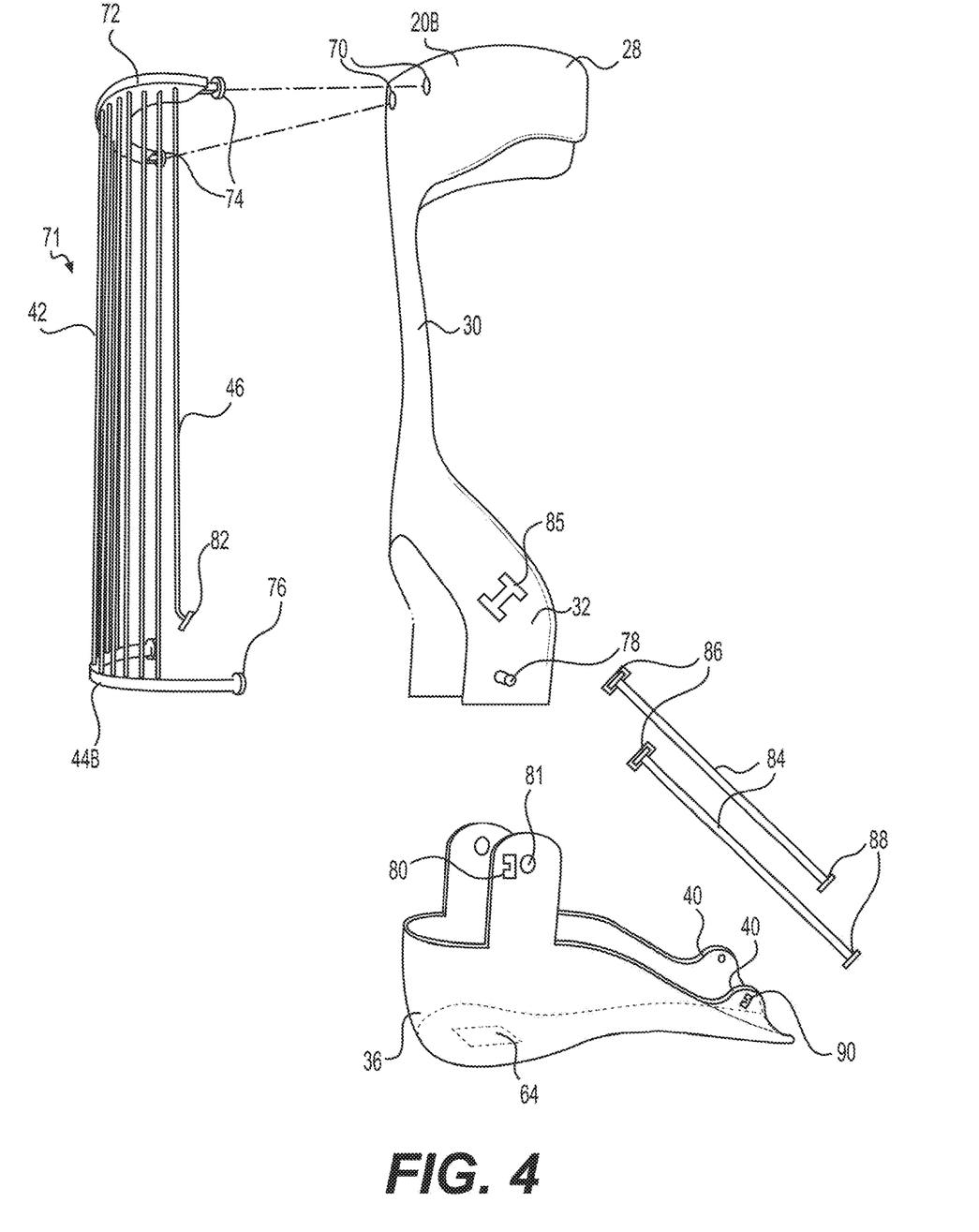
FIG. 4 includes a schematic illustration of modular components of an exemplary orthotic device of the present disclosure.

It should be understood that the disclosed orthotic devices 10, 10*a*, 10*b* are exemplary and that other configurations are possible, such as to incorporate alternative or additional features. FIGS. 3 and 4 depict such features. FIG. 3 depicts, for example, an alternative pivot member 44A and alternative second actuators 46A. It should be understood that either or both of these features may be incorporated into orthotic device 10.

As shown in FIG. 3, pivot member 44A may include an alternative shape that allows actuator 42 to be connected to pivot member 44A at a higher location that pivot member 44A, while maintaining the same pivot point at pivot mechanism 34. For example, pivot member 44A may include a "Z" or "L" shape to allow the higher connection point to maintain control over pivoting of heel cup 36 via pivot mechanism 34. The higher connection point allows for shorter strands 52 and also allows for additional space behind a user's ankle such that a wider array of normal-sized shoes may be worn without interference from pivot mechanism 36.

Second actuators 46A may be similar to second actuators 46, except that an upper portion of second actuators 46A may be anchored a connection portion 26 of leg holder 20, instead of upper attachment portion 22. This allows for shorter strands 54 and more responsive control of heel cup 36. As shown in FIG. 3, controller 66 may be disposed at connection portion 26 for a more convenient connection to both first actuators 42 and second actuators 46A (or may be a second controller that complements the controller located near upper attachment portion 22).

FIG. 4 depicts an orthotic device 10 including modular features that may be selectively connected and disconnected from each other. Orthotic device 10 includes a leg holder 20B, a modular actuator 71, heel cup 36, and connection bands 84. Leg holder 20B may be the same as leg holder 20, except that leg holder 20B may include features that allow for selective connection to modular actuator 71 and/or heel cup 36. For example, leg holder 20B may include connectors 70 and 78.

Modular actuator 71 may be similar to actuating system 14 of FIG. 1. However, modular actuator 71 may include an upper connection member 72 configured to be secured to an upper end of first actuator 42 and second actuator 46. Upper connection member 72 may include connectors 74 configured to be secured to connectors 70 of leg holder 20B. For example, connectors 74 may be projections configured to be secured in connectors 70, which may be apertures. In this way, modular actuator 71 may be anchored to an upper portion of leg holder 20B.

Modular actuator 71 may also include features that allow for connection to heel cup 36. For example, modular actuator 71 may include a pivot member 44B, which may be attached to the lower end of first actuator 42. Pivot member 44B may be the same as or similar to pivot member 44, except pivot member 44B may include connectors 76 configured to be secured to first connectors 38 on heel cup 36. Heel cup 36 may include corresponding connectors 80, which may receive connectors 76. Heel cup 36 may also include pivot connectors 81 configured to be secured to connectors 78 of leg holder 20B, to rotatably secure heel cup 36 to leg holder 20B.

Modular actuator 71 may also be configured to connect second actuator 46 to heel cup 36. In an exemplary embodiment, second actuator 46 may include a connector 82 configured to removably connect second actuator 46 to second connectors 40 of heel cup 36. In the embodiment of FIG. 4, connection bands 84 may connect second actuator 46 to second connectors 40. Connection bands 84 may be intermediate connectors configured to a distance between second actuator 46 and second connectors 40. Connection bands 84 may be elastic or non-elastic members that translate motion from second actuators 46 to second connectors 40. While described in relation to FIG. 4, it should be understood that that connection bands 84 may be implemented with any embodiment of orthotic device 10 (e.g., the embodiment of FIG. 1). Further other mechanism, such as torsion springs may be used to translate movement of actuator 46 into movement of second connectors 40.

Connection bands 84 may include connectors 86, 88 at opposing ends. Connectors 82 may be secured to connectors 86 and connectors 88 may be secured to connectors 90 at second connectors 40. An attachment member 85 may hold connectors 82 and 86 close to a surface of heel cup 36, while allowing for translational movement of connection bands 84. In use, actuating movement of second actuator 46 will cause rotational movement of second connectors 40 by pulling on connection bands 84.

Through the above described connection mechanisms, various modular components of orthotic device 10 may be removably secured to each other, in this way, selected combinations components may be easily assembled to create an orthotic device that is adapted to the needs of a particular user. For example, a leg holder 20B adapted for use with a particular user's leg may be connected with a heel cup 36 that is sized to fit that user's foot. Further, these modular components allow for replacement, as necessary. For example, one or more components may be interchanged as a user grows, for example.

Further, it should be understood that one or more of the components of orthotic device 10B may be used with orthotic device 10. For example, connection bands 84 may be used to secure second actuator 42 to second connectors 40. In this way, it may be unnecessary for actuator 42 to extend from an upper portion of leg holder 20 to second connectors 40, and, instead, connection bands 84 can serve as replacement intermediary devices that translate pulling forces from second actuator 42 to heel cup 36.

Figure 5:
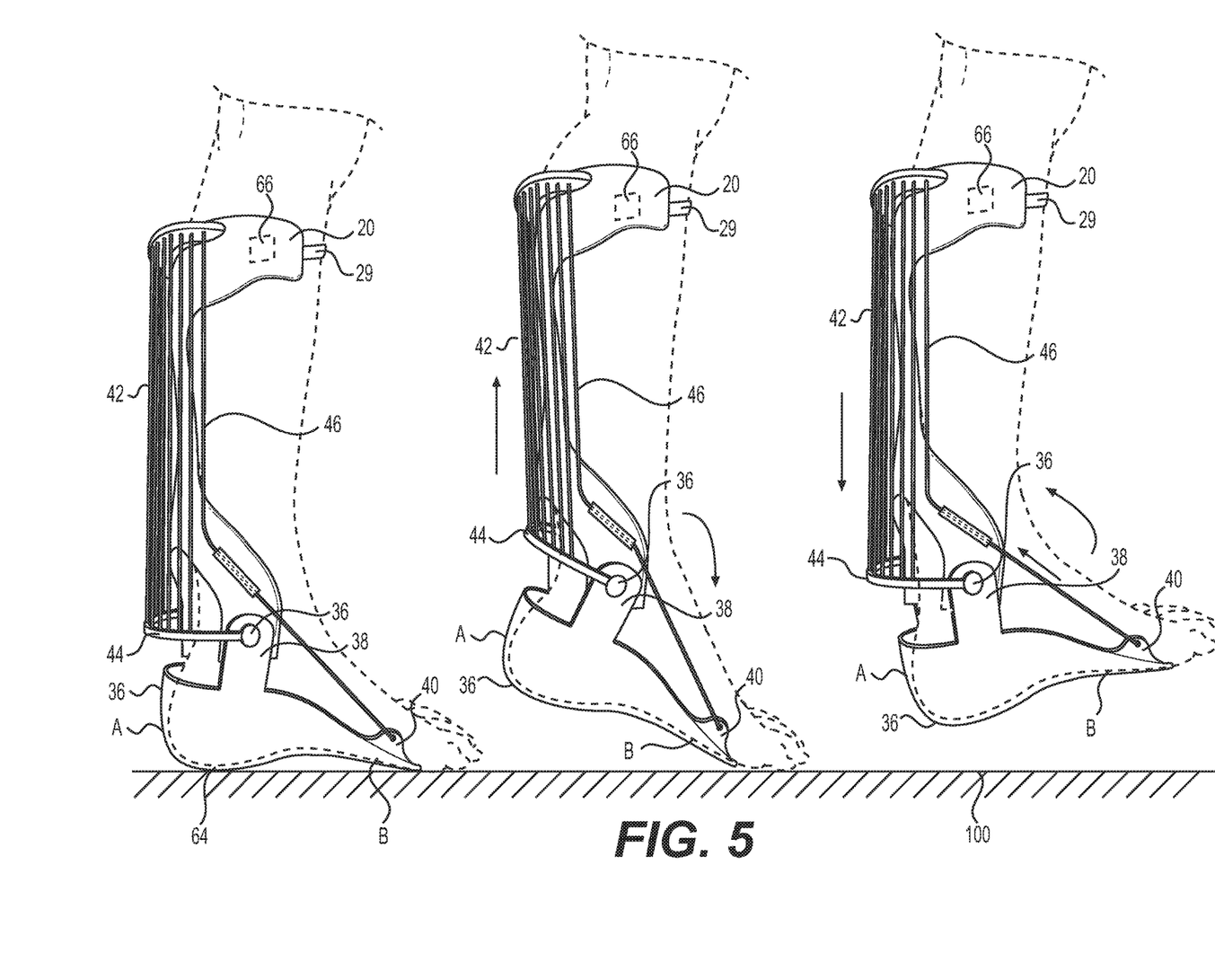
FIG. 5 includes illustrations of an orthotic device of the present disclosure at various stages during use.

As described above, an orthotic device of the present disclosure may aid a user in movement of a limb. For example, the orthotic device may cause a user's limb to mimic normal functioning movement, even though the limb may be incapable of functioning on its own. In one example, the disclosed orthotic device provides a walking aid for a user suffering from drop foot or any gait abnormality. FIG. 5 depicts a user at various steps of walking while using orthotic device 10, as described in more detail below. The insertable orthotic devices 10b, 10c function similarly.

INDUSTRIAL APPLICABILITY

The disclosed orthotic device may provide a new solution for people that suffer from a condition that causes one or more limbs to be unable to function normally. The disclosed orthotic device may be particularly applicable to correct gait abnormalities, helping to return a user's debilitated lower leg and foot to normal functioning and/or operation. In one embodiment, the disclosed orthotic device utilizes electroactive fibers as an artificial muscle actuator. The electroactive fibers are strong, yet thin, providing high-quality performance in a small space. The thin actuators, in combination with a heel cup design that fits within a normal-sized shoe and an ergonomic attachment mechanism, allows for a compact design that may be concealed underneath a user's normal clothing, which may be appealing to many potential users.

A user may prepare for use of orthotic device 10 by positioning frame system 12 at appropriate locations. For example, the user may place their foot inside heel cup 36, insert the back side of their lower leg in leg holder 20, and tighten strap 29. The user may wear normal clothing over orthotic device 10, including placing their foot in a shoe and allowing a pant leg to cover leg holder 20 and actuating system 14, if desired. In some instances, a user may wear an orthotic device 10 on both legs, such as to assist movement of both legs.

In some instances, the user may also take steps to position one or more sensors 64. For example, in one embodiment, sensor 64 may be placed within a shoe that the user wears on their other foot (e.g., the foot of the user's good leg). In another example, a sensor may be positioned at another location on the user's body, such as at the user's knee, waist, chest, head, etc. The sensor may be positioned at the particular location via placement within an article of clothing, such as a shirt, hat, watch, etc.

FIG. 5 depicts a user's leg throughout three different stages of walking using orthotic device 10. While the user is shown wearing only orthotic device 10, it should be understood that the user may wear clothing over orthotic device 10, if desired. For example, a stocking may envelope orthotic device 10 such that it is substantially concealed from view. The user may additionally or alternatively wear shoes and/or pants that cover at least a portion of orthotic device 10. The orthotic device 10a, 10b is configured to be inserted into footwear, concealed from normal view, and function similar to the embodiments shown in FIGS. 1-5. As shown, a first portion A of the user's foot may correspond to the user's heel while a second portion B may correspond to the toe portion of the user's foot. The user may stand upright and prepare to walk with their foot flat on the ground, as shown at the first stage of FIG. 5.

With a normal functioning leg and foot, a user may walk forward by pushing off to lift the heel off of the ground, shifting their weight to the ball of the foot. As the user shifts weight to their other leg, the user may lift the front of their foot off of the ground, such that the entire foot can be brought forward for the next step. Orthotic devices 10, 10a, 10b, via actuating system 14, 14a, 14b, may replicate this motion so that the user regains substantially normal operation of the limb.

Actuating system 14, 14a, 14b may be actuated and provide assistance to a user to help lift their foot off of the ground during walking. Control system 48 may control actuating system 14, 14a, 14b to determine how and when to provide the assistance. Sensor 64, 64a, 64b may, for example, sense when the user's foot hits the ground, and may send this information to controller 66, 66a, 66b. Controller 66, 66a, 66b may make a determination that the user is walking forward. For example, sensor 64, 64a, 64b may sense a shift in the foot indicative of forward movement. This may include a change in foot placement or a change in acceleration of the user. Based on this determination, controller 66 may activate first actuator 42 and apply an upward pressure to portion A. This may lift portion A of the user by rotating pivot member 44 and heel cup 36, causing the user's heel to raise off the ground, as shown in the second stage of FIG. 5.

A forward walking motion of the user and the lift of portion A may push off the user's forefoot (portion B) from the ground. In some embodiments, controller 66, 66a, 66b may receive additional information from sensor 64, 64a, 64b, and may further determine that the user's heel is off the ground and the user has pushed off from the ground with the user's forefoot. In the embodiment shown in FIGS. 1-5, controller 66 may then deactivate first actuator 42.

At this time, controller 66, 66a, 66b may activate actuator 43a, 43b, 46 and apply an upward pressure to portion B. This may lift portion B, causing the user's forefoot to raise upward and away from the ground, as shown in the third stage of FIG. 5. Upward movement of portion B may raise the user's toes upward, and may prevent the user from tripping on the toes when walking forward. Controller 66 may activate actuator 43a, 43b, 46 when the user's toes are still on the ground, allowing the toes to pivot upward when the user is moving forward.

Pivot mechanism 34 may allow frame system 12 to rotate and move with the user during this walking step, mimicking the fore/aft rotation of the user's ankle. Second actuator 46 may remain actuated until the user's foot again steps down on the ground, for example when sensor 64 detects the user's foot on the ground. Controller 66 may then deactivate second actuator 46, and continue the cycle by activating first actuator 42 to raise the user's heel.

Controller 66, 66a, 66b may determine that the user intends to walk faster or slower. For example, controller 66 may receive a signal from sensor 64 indicating that the user has changed body motion or orientation. Based on this signal, controller 66 may determine the user's intentions and may activate first and second actuators 42, 46 accordingly. In one example, controller 66 may receive a signal from sensor 64 that the user is leaning forward and may determine that the user desires to walk faster. Controller 66 may then activate and deactivate first and second actuators 42, 46 in a faster cycle to increase the walking speed of the user.

In some embodiments, controller 66, 66a, 66b may determine that the user intends to turn to the left or right, and may activate actuators 42, 43a, 43b, 46, respectively. In other embodiments, controller 66 may determine that the user does not wish to move forward. For example, sensor 64 may detect a substantial majority of the user's weight on the user's heel, rather than substantially even distributed across the user's foot. In this example, controller 66 may determine the user wishes to remain in place and may not activate actuators 42, 46.

In an exemplary embodiment, actuators 42, 43a, 43b, 46 may be electronically actuated muscles in the form of electroactive polymers. The electroactive polymers may be in the form strands 52, 54, which may be bundles of fibers 58 within an outer sleeve 60, as shown in FIG. 2 Controller 66, 66a, 66b may activate the electroactive polymers by, for example, applying or removing a voltage to an electrode (e.g., water) inside outer sleeve 60. This may cause the electroactive polymers to deform and axially shorten or lengthen. Controller 66, 66a, 66b may additionally discontinue the voltage and deactivate the electroactive polymers based on a signal received from sensor 64, 64a, 64b, Controller 66, 66a, 66b may independently activate and deactivate actuators 42, 43a, 43b, 46 causing actuators 42, 43a, 43b, 46 to independently deform.

It should be understood that other actuating elements may be used. For example, some embodiments may include actuators 42, 43a, 43b, 46 comprised of nanotechnology, ferro-fluid, magnetorheological electorheological fluid, piezoelectric polymers, electrostatic device, rotary motors, linear actuators, and pneumatic actuators. In one embodiment, actuators 42, 43a, 43b, 46 may include artificial muscle comprised of nanomaterials acting as an artificial muscle outside of a user's body. Additionally, any actuating process may be used that is suitable for an orthotic device.

While sensor 64 within orthotic device 10 is described with respect to FIG. 5, it should be understood that other configurations of sensor 64 may similarly be used to cause controller 66, 66a, 66b to activate and deactivate actuators 42, 43a, 43b, 46. For example, sensor 64 may be positioned on the user's other leg (e.g., the user's good leg) and transmit signals to controller 66 based on the motion of the user's good leg such that orthotic device 10 substantially mirrors the movement of the user's good leg. In other embodiments, the user may provide manual input to control actuators 42, 43a, 43b, 46. For example, sensor 64, 64a, 64b may be voice-actuated, or may include a hand-held device for allowing control by the user.

In some embodiments, control system 48 may include a plurality of modes that may be selected by the user. For example, control system 48 may include a walking mode and a rehabilitation mode. The walking mode may correspond to the walking function described above or other normal-use function of a limb. The rehabilitation mode, on the other hand, may correspond to a mode in which control system 48 causes actuators 42, 43a, 43b, 46 to activate and deactivate while the corresponding limb (e.g., the user's foot) is off the ground. This may stretch the user's muscles, helping to strengthen the limb for future use and avoid atrophy due to non-use of the limb.

The orthotic device of the present disclosure may help people regain normal functioning and/or operation of their limbs. In one implementation, the orthotic device may respond to a user's movement and may provide an actuating force to help the user's foot off the ground, creating a more normal walking gait. Additionally, the orthotic device has a compact and lightweight design and, in the embodiments shown in FIGS. 6-15, may be concealed within the user's shoe. Therefore, users requiring orthotic support may be more willing to wear the device. Further, the orthotic device may provide for additional features, such as a rehabilitation mode in which a user may stretch and move their muscles even when the user is otherwise inactive.

It will be apparent to those skilled in the art that various modifications and variations can be made to the orthotic device of the present disclosure without departing from the scope of the disclosure. Other embodiments will be apparent to those skilled in the art from consideration of the specification and practice of the embodiments disclosed herein. It is intended that the specification and examples be considered as exemplary only, with a true scope of the disclosure being indicated by the following claims.

What is claimed is:

1. An orthotic device for a foot adapted to be inserted into a shoe along a bottom portion of the foot to enable the foot to replicate normal motion so that the user regains substantially normal functioning of the foot, the orthotic device comprising:
   a frame system having a base portion including a heel portion, formed of a lightweight supportive material and configured to extend along at least the bottom portion of the foot, wherein the frame system includes a substantially rigid base portion and a toe portion that is adapted to move relative to the base portion;
   an electronically actuated muscle operatively connected to the frame system for expanding and contracting at predetermined levels to adjust the inclination of the foot and mimic movement of the foot when functioning normally;
   a controller operatively connected to the muscle for transmitting signals corresponding to the predetermined levels to the muscle; and
   a sensor controlled by the user for actuating the muscle.

2. The orthotic device as defined in claim 1, wherein the frame system includes a heel portion, a midfoot portion and a toe portion, and wherein the frame system is flexible at least along a toe portion so that the toe portion lifts in response to actuation of the muscle.

3. The orthotic device as defined in claim 1, wherein the frame system includes a substantially rigid base portion and a toe portion that is adapted to move relative to the base portion.

4. The orthotic device as defined in claim 1, wherein the electronically activated muscle extends between a connector at the heel portion to a guide near a toe portion when the muscle has not been activated, and wherein the muscle is adapted to expand longitudinally when activated by the controller to engage the toe portion and lift the user's toe.

5. The orthotic device as defined in claim 1, wherein the frame system includes a downward projection along a bottom surface of the toe portion for engaging muscle to lift and lower the toe portion in response to signals from the controller.

6. The orthotic device as defined in claim 1, wherein the frame system is concealed from view once inserted in a shoe.

7. The orthotic device as defined in claim 1, wherein the frame system includes an upper layer formed of high density foam.

8. The orthotic device as defined in claim 1, wherein the frame system is formed of a fiber-reinforced polymer.

9. The orthotic device as defined in claim 1, wherein the frame system includes a base portion and a toe portion, and wherein the muscle is an arrangement of electroactive polymer strands connecting the heel portion of the frame system to the toe portion.

10. The orthotic device as defined in claim 9, wherein the muscle also includes conductive caps for securing opposite ends of the arrangement of electroactive polymer strands, and a fluid-filled sleeve enveloping the polymer strands and extending between the conductive caps.

11. The orthotic device as defined in claim 1, wherein the controller contains algorithms corresponding to various modes of operation.

12. The orthotic device as defined in claim 11, wherein the controller can be adjusted to generate signals corresponding to more than one mode of operation.

13. The orthotic device as defined in claim 11, wherein one mode corresponds to the user's normal gait.

14. The orthotic device as defined in claim 13, wherein another mode is for rehabilitative movement.

15. The orthotic device as defined in claim 11, wherein the sensor is adapted to be positioned on the user's good leg so that the orthotic device substantially mirrors the movement of the user's good leg.

16. The orthotic device as defined in claim 1, wherein the sensor is wireless and adapted to actuate the muscle in response to predetermined movement by the user.

17. The orthotic device as defined in claim 1, wherein the sensor is voice-activated.

18. The orthotic device as defined in claim 1, wherein the sensor is actuated by a hand-held device.

19. The orthotic device as defined in claim 1, wherein the frame system, muscle and controller are integrally formed as a one piece shoe insert adapted to operate by a remote sensor.

* * * * *